United States Patent
Vasarhelyi et al.

(10) Patent No.: US 9,107,675 B2
(45) Date of Patent: Aug. 18, 2015

(54) DEVICE FOR IN SITU MILLING OF JOINT SURFACES

(75) Inventors: Attila Vasarhelyi, Leipzig (DE); Rolf Hartmann, Boras (SE)

(73) Assignee: UNIVERSITÄT ROSTOCK, Rostock (DE)

( * ) Notice: Subject to any disclaimer, the term of this patent is extended or adjusted under 35 U.S.C. 154(b) by 791 days.

(21) Appl. No.: 13/381,184

(22) PCT Filed: Jun. 16, 2010

(86) PCT No.: PCT/EP2010/003620
§ 371 (c)(1),
(2), (4) Date: Dec. 28, 2011

(87) PCT Pub. No.: WO2011/000476
PCT Pub. Date: Jan. 6, 2011

(65) Prior Publication Data
US 2012/0109131 A1    May 3, 2012

(30) Foreign Application Priority Data
Jun. 30, 2009  (DE) .......................... 10 2009 031 269

(51) Int. Cl.
| A61B 17/16 | (2006.01) |
| A61B 17/17 | (2006.01) |
| A61B 17/15 | (2006.01) |
| A61B 17/02 | (2006.01) |

(52) U.S. Cl.
CPC ................. *A61B 17/15* (2013.01); *A61B 17/16* (2013.01); *A61B 17/1682* (2013.01); *A61B 17/025* (2013.01); *A61B 2017/1602* (2013.01); *A61B 2017/1775* (2013.01)

(58) Field of Classification Search
USPC .................................................. 606/79, 88, 90
See application file for complete search history.

(56) References Cited

U.S. PATENT DOCUMENTS 5,041,119 A * 8/1991 Frigg et al. ...................... 606/96
2010/0274251 A1   10/2010 Ranft

FOREIGN PATENT DOCUMENTS

| DE | 10215358 B4 | 3/2007 | |
| DE | 102008039241 A1 | 5/2009 | |
| EP | 1374783 A1 | 1/2004 | |
| WO | 01/66021 A1 | 9/2001 | |
| WO | WO 0166021 A1 * | 9/2001 | ............. A61B 17/14 |
| WO | 2007/130467 A2 | 11/2007 | |
| WO | 2008/043380 A1 | 4/2008 | |

* cited by examiner

*Primary Examiner* — Christian Sevilla
(74) *Attorney, Agent, or Firm* — Rankin, Hill & Clark LLP (57) ABSTRACT

A device for in situ milling of joint surfaces, including a milling device and a joint clamping device. The joint clamp device is designed to be inserted between two joint components forming a joint, particularly bones, and for pushing the joint components apart with a predetermined or adjustable tension, wherein the joint clamping device includes a recess in which the milling device can be inserted, wherein the milling device includes a face milling cutter.

18 Claims, 8 Drawing Sheets

DEVICE FOR IN SITU MILLING OF JOINT SURFACES

The invention relates to a device for in situ milling of joint surfaces, comprising a milling device and a joint-tensioning device. The invention further relates to a use of a corresponding device, and to a method for in situ milling of joint surfaces.

Arthrosis is a chronic degenerative disease of the joints and is characterized by breakdown and transformation of the articular cartilage. Arthrosis develops as a result of a disparity between the demands placed on the affected joint components and the performance of these joint components. Arthrosis can be aggravated by inherited or acquired previous damage. The wear and attrition of an articular cartilage increasingly limits the function of the latter and leads among other things to pain on movement and to pain following exercise.

Established conservative therapies for alleviating the symptoms caused by diseased joints are unsuccessful in severe cases. In such cases, surgery performed on the joint using an artificial joint replacement, or endoprosthesis, is indicated. As regards endoprostheses, a distinction can be made between surface replacement endoprostheses, partial endoprostheses and total endoprostheses.

Depending on the anatomical circumstances of a particular joint or joint type, certain bone and cartilage components are removed and subsequently replaced by prosthetic material. The operating surgeon has to estimate the amount of the skeletal structures to be removed in order to ensure satisfactory biomechanical functioning of the joint after insertion of the prosthesis components. This proves difficult to calculate especially in the case of joints functioning in the manner of a hinge, e.g. the knee joint, the elbow joint or the ankle joint.

An aim of such operations is to position the prosthesis in such a way that the original axial kinematics and ligament guidance of the affected joint are restored, in order to permit sufficient mobility of the joint and also good stability in the different positions the joint has to assume. If these conditions are not met, the function of the joint is impaired. Because of increased shearing forces on the prosthesis material, this also leads to increased wear and, in some case, early loosening of the artificial joint. This results in premature or early failure of the artificial joint, and the latter needs to be replaced before time.

In order to prepare the bone of the joint for the insertion of an artificial joint, it is first of all necessary to shape the skeletal structures on which the components of the artificial joint can subsequently be implanted.

In order to prepare skeletal structures, saw blocks are in many cases firstly positioned with the aid of orientation jigs, and these saw blocks serve as templates for resections of bone substance. Along the shape defined by the saw blocks, a bone is cut through near the affected joint with the aid of oscillating saws, and one or more resection surfaces are produced on the bone.

The saw cuts are carried out in previously defined positions of the joint, e.g. in a neutral position and mid-position. If appropriate, further saw jigs are then placed on the bone surface obtained, and the bone is worked again in order to obtain a desired surface profile onto which a sample prosthesis can be mounted with an exact fit to replace the previous joint surface. After the preparation of the bone has been completed, the prosthesis components made of a special metal alloy are implanted on the respective resected surfaces. A sliding core made of highly crosslinked plastic is placed between the metal components.

The artificial joint inserted in this way is not adapted to the existing ligaments that hold the joint. By using different thicknesses of the sliding core, there is still some potential for correction. However, there is the danger of the joint being insufficiently stable.

The described method is improved, for example in surgery of the knee joint, by using so-called joint-tensioning devices. A corresponding joint-tensioning device is known from WO 2008/043380 A1. In this known joint-tensioning device, pairs of elongate arms, so-called claws, are pushed between the bones into the joint. The claws are pressed apart with an adjustable force, and the joint and the ligaments of the joint are thus tensioned. With the aid of such joint-tensioning devices, it is possible to perform the resection of skeletal components with an oscillating saw in one or more different joint positions under defined tensioning conditions of the soft-tissue parts of the joint. This results in a prosthetic joint that is better balanced with respect to the soft-tissue parts of the joint. It is possible in this case to predict the tensioning conditions or spacing conditions between the prosthesis components for the defined joint positions in which the bone cuts have been made.

For skeletal resection, straight saw blades are normally used, such that the finally prepared skeletal body presents the shape of a polyhedron.

WO 2007/130467 A2 describes a device and a method in which a resection of skeletal components of a joint is performed with the aid of roller-shaped millers inserted into the joint space or with the aid of an endless-belt-type device. In these milling cutters, the rotation axes of the rollers or of the endless-belt device lie parallel to the resected joint surface.

According to WO 2007/130467 A2, the resection of the convex joint surface is performed, in order to generate a convex resection surface, by "swinging" through the joint several times along its relevant movement plane. A joint moved in the manner of a hinge is rotated several times about its joint axis for this purpose, the joint being held by the ligaments that are present. The resulting resection surfaces are curved surfaces on account of the swing-through of the joint.

The milling device disclosed in WO 2007/130467 A2 has expandable units by means of which the pressure of the milling device on the joint surface is determined. In roll milling or endless-belt grinding, forces act on the cartilage or bone that is to be resected and influence the desired orientation. Failings in the resection result are minimized by the contact pressure of the cutter being kept low. Since the joint has to be swung through often during the milling procedure using a low contact pressure, this entails a correspondingly longwinded operating process.

Proceeding from this prior art, the object of the invention is to make available a device and a method for in situ milling of joint surfaces, particularly but not exclusively of joints that function in the manner of a hinge, by means of which device and method it is possible for joint surfaces to be prepared quickly and safely for implantation of endoprostheses, with the original axial kinematics and ligament guidance being optimally restored.

This object is achieved by a device for in situ milling of joint surfaces, comprising a milling device and a joint-tensioning device, wherein the joint-tensioning device is designed to be inserted between two joint components forming a joint, particularly bones and/or joint-forming slide surfaces, and to press the joint components, particularly bones, apart with a predetermined or adjustable tension, wherein the joint-tensioning device has a recess into which the milling device can be inserted, wherein the milling device has a face milling cutter.

In the context of the invention, a face milling cutter is understood to mean a cutter whose rotation axis is perpendicular or substantially perpendicular to the surface that is to be milled. The milling device is a functional unit.

The invention achieves a number of effects related to one another. A first effect lies in the decoupling of the joint-tensioning device and the milling device in the device according to the invention. As a result of this decoupling, it is possible, as the joint is swung through, and in each position of the joint, to adopt a joint tension that is predetermined by the joint-tensioning device or is adjustable and that can simulate a natural tension of the joint, independently of the contact pressure of the milling device.

As a result of this decoupling, it is possible for the existing axial kinematics defined by the ligaments to be reproduced more exactly than was possible in the prior art, for example according to WO 2007/130467 A2. According to the invention, it is no longer necessary to minimize a contact pressure and, consequently, the tensioning of the joint and to therefore accept that the existing axial kinematics will be reproduced only inexactly because of the resulting low tension of the ligaments.

A further effect of the invention, related to the first effect, arises from the use of a face milling cutter. By using a face milling cutter instead of roller cutters, the forces or shearing forces that act on the joint during milling are considerably reduced. This permits an increase in the contact pressure.

Since the joint tension is predefined by the joint-tensioning device and since a face milling cutter can be used with greater contact pressure than was hitherto possible and, in addition, the depth of penetration of a face milling cutter is greater than the depth of penetration of the known device, it is thus possible to produce a resection surface with only a few swings of the joint, preferably with just one swing of the joint. The face milling cutter can preferably be shaped in such a way that the desired depth of the milled surface is already obtained in one work step. In this way, the time needed for the operation is greatly reduced.

The face milling cutter preferably has milling surfaces both on its face and also on its periphery. Moreover, the face milling cutter preferably has a curved milling profile. In this way, it is possible for a deep milling or resection surface to be generated in one go with the face milling cutter, by lateral advance of the milling device, that is to say an advance transverse to the rotation axis of the face milling cutter, or by means of a hinge movement of the joint.

The milling device advantageously has a chassis for the face milling cutter, which chassis can be inserted into the recess of the joint-tensioning device and/or can be fixed in the recess of the joint-tensioning device. The chassis preferably has the external dimensions of the recess, such that it can be arranged in the joint in a manner secure against sliding or shifting.

In an advantageous embodiment, the milling device can be driven by means of a gearwheel drive with toothed wheels, wherein one toothed wheel is connected to the face milling cutter or is formed in one piece with the face milling cutter, and another toothed wheel, which meshes in the toothed wheel connected to the face milling cutter or formed in one piece with the face milling cutter, is connected to a spindle. The spindle is preferably connected to a drive device. The drive device can be a manual drive or an electric drive, it being particularly advantageous for the drive speed to be controllable. By means of the gearwheel drive, the face milling cutter can be driven efficiently, taking up minimal space, with its rotation axis perpendicular to the joint surface.

The joint-tensioning device is preferably hydraulic and/or designed with claws which, in the state when inserted into a joint, bear on joint parts. A device using claws is known from WO 2008/043380 A1, for example.

Alternatively or in addition to this, in a preferred embodiment the joint-tensioning device is designed as a one-piece or multi-piece elastomer body or comprises one or more elastomer bodies. By means of an elastomer body, the joint is oriented according to the joint tension. It is thus possible, in each position of the joint, to generate a defined pressure that is independent of the contact pressure of the milling device. Several elastomer pieces or elastomer bodies can serve as bearing surfaces for claws.

The joint-tensioning device, in particular the elastomer body, preferably has a bearing surface for a resection surface of a bone. In this way, the elastomer body or the joint-tensioning device can be inserted into the enlarged space and placed on the resection surface of the bone, which already has, for example, a flat resection surface.

According to the invention, the joint-tensioning device, in particular the elastomer body, advantageously has a shaft-shaped recess into which a milling device can be inserted. The recess preferably has means for mounting, guiding and/or fixing a milling device.

To the sides of the recess, the joint-tensioning device, in particular the elastomer body, preferably has support surfaces for supporting on a bone that is to be resected. These support surfaces thus delimit the recess on both sides. Particularly in the case where the further bone to be resected has a convex joint surface, the support surfaces have concave curvatures for receiving curved parts of the bone. The concave curvatures of the support surfaces thus serve to guide the further bone to be resected, or the further joint components to be resected, during the swing-through of the joint and prevent the bone or the joint body from coming out of position during the milling.

The device advantageously comprises a base unit, which can be fixed on a bone and which has means for mounting the joint-tensioning device. Such a base unit can also be used for mounting saw templates, etc. In particular, the joint-tensioning device, in particular the elastomer body, advantageously has openings or means for mounting on the base unit and/or for engagement with holding means of the base unit.

The object of the invention is further achieved by the use of an above-described device according to the invention for in situ milling of joint surfaces.

The object of the invention is likewise achieved by a method for in situ milling of joint surfaces by means of an above-described device according to the invention, with the following method steps:

pushing a joint-tensioning device in between the bones or joint components adjacent to the joint, of which one bone or joint component is already resected, wherein the joint is subjected to a predetermined or adjustable tension, inserting a milling device with a face milling cutter into a shaft recess of the joint-tensioning device, wherein in particular the face milling cutter is driven during the insertion in order to form a resection surface on the hitherto non-resected bone or joint component, producing a curved resection surface on the hitherto non-resected bone or joint component by swinging the joint through, in particular once.

It is thus possible to produce a curved resection surface very quickly while preserving the original axial kinematics and ligament guidance of the joint.

Advantageously, a resection surface is produced beforehand on the bone, in particular by placing a base unit on a bone adjacent to a joint and mounting a saw jig onto the base unit.

Moreover, the saw jig is preferably removed from the base unit after a resection surface has been produced on the bone.

Finally, after a curved resection surface has been produced, the milling device and the joint-tensioning device are preferably removed from the joint. Lateral bone remnants, on which the joint-tensioning device had previously rested, can then be removed in order to obtain a final curved resection surface. In certain types of joints (e.g. ankle joint), the joint surfaces on which the joint-tensioning device had previously rested are removed in order to ensure that the corresponding joint component can be covered completely with the prosthesis.

The invention is described below on the basis of illustrative embodiments and with reference to the drawings, without limiting the general concept of the invention. As regards all the features according to the invention that are not explained in detail in the text, reference is made expressly to the drawings, in which:

FIG. 12 shows a schematic side view of the arrangement according to FIG. 11.

In the attached figures, the same or similar elements or corresponding parts are provided in each case with the same reference signs and are therefore not presented anew on each occasion.

Figure 1:
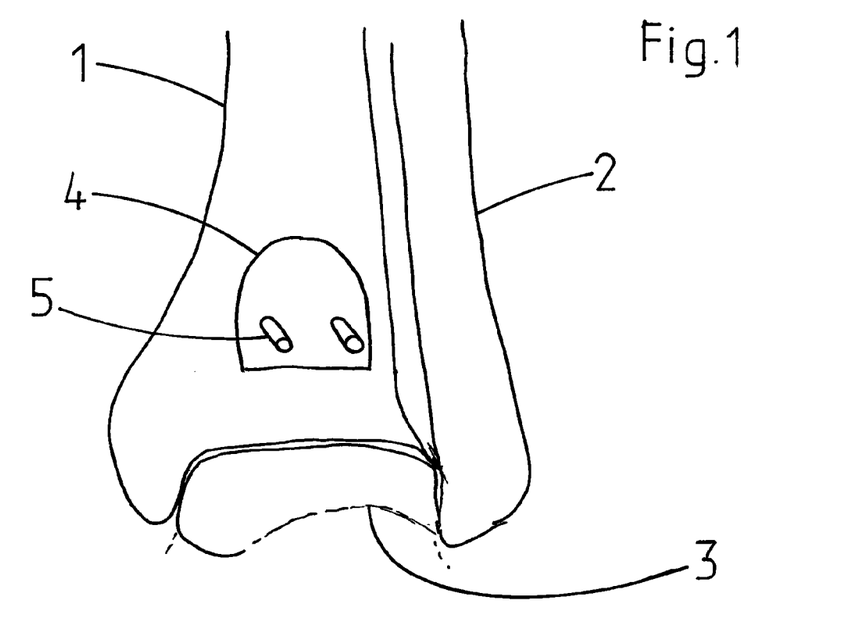
FIG. 1 shows a schematic rear view of an ankle joint with a base unit.

FIGS. 1 through 15 show, in each case in highly schematic views, the sequence of a bilateral joint resection, using the example of an ankle joint. FIG. 1 shows a schematic rear view of an ankle joint with shinbone 1 (tibia), calf bone 2 (fibula) and ankle bone 3 (talus). In FIG. 1 and in the following figures, the ankle bone 3 is shown only partially by the joint head.

A base unit 4 is fixed on the posterior face of the shinbone 1 and has pins 5 serving as means for mounting saw jigs, joint-tensioning devices, etc., which are set out below.

Figure 2:
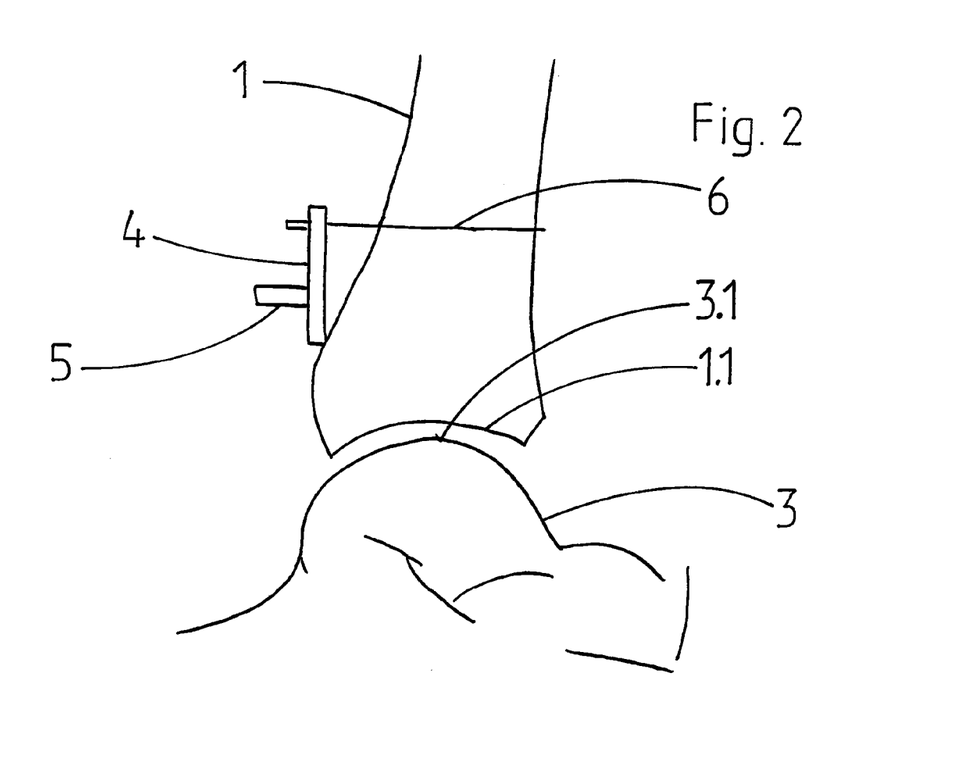
FIG. 2 shows a schematic side view of the arrangement according to FIG. 1.
Figure 3:
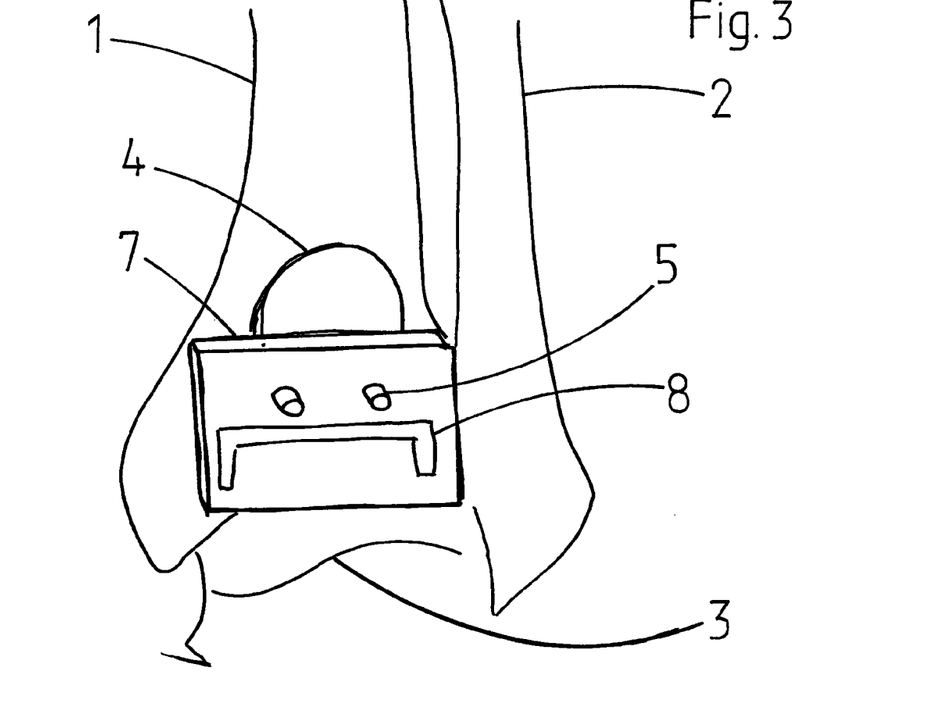
FIG. 3 shows a schematic rear view according to FIG. 1 with a saw jig placed on the base unit.

FIG. 2 shows a schematic side view of the view according to FIG. 1. It additionally shows a holder 6, by means of which the base unit 4 is screwed or anchored in the shinbone 1. The base unit 4 is connected fixedly to the shinbone 1 and thus provides a constant reference point for the subsequent cuts and milling movements. The figure also shows a concave joint surface 1.1 of the shinbone 1 and a convex joint surface 3.1 of the ankle bone 3. In the next step, which is shown in FIG. 3, a saw jig 7 has been fitted onto the pins 5 of the base unit 4. The saw jig 7 has a slit 8, which has the shape of an inverted U and which defines a resection surface with three sections for the shinbone 1. Lateral parts of the shinbone 1 are thus preserved during the resection.

An oscillating saw blade (not shown) is pushed through the slit 8 in order to make a corresponding cut and produce a resection surface 1.2.

Figure 4:
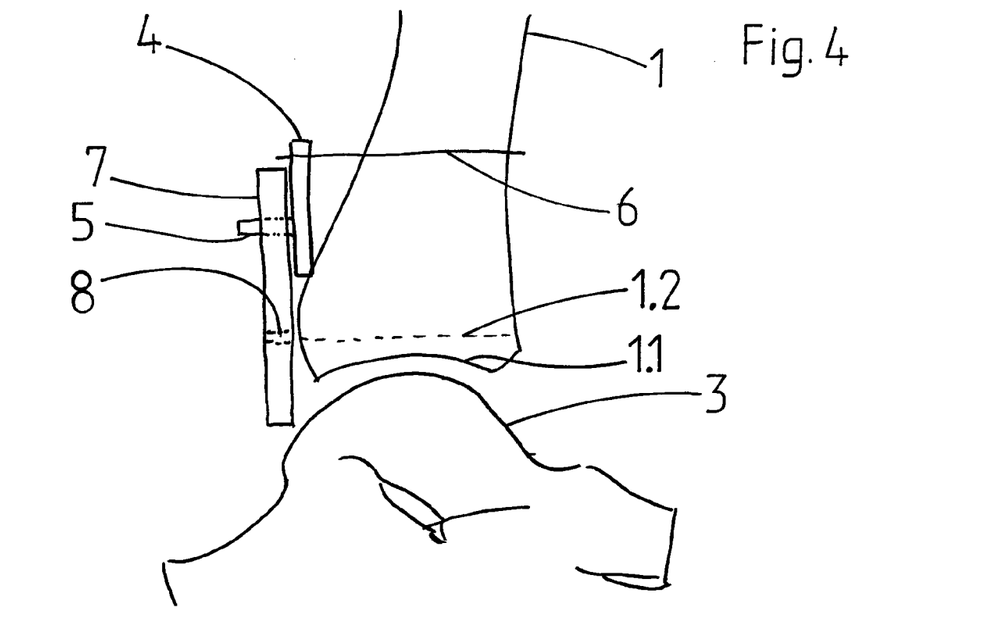
FIG. 4 shows a schematic side view of the arrangement according to FIG. 3.

The planned resection surface 1.2 on the distal end of the shinbone 1 is indicated by a broken line in FIG. 4 in a side view. FIG. 4 shows a sectional view perpendicular to the viewing surface from FIG. 3, which runs approximately through the pin 5 from FIG. 3, which is likewise shown in FIG. 4. It can clearly be seen that the resection surface 1.2 on the shinbone 1 is set back from the concave joint surface 1.1 and is straight or flat.

Figure 5:
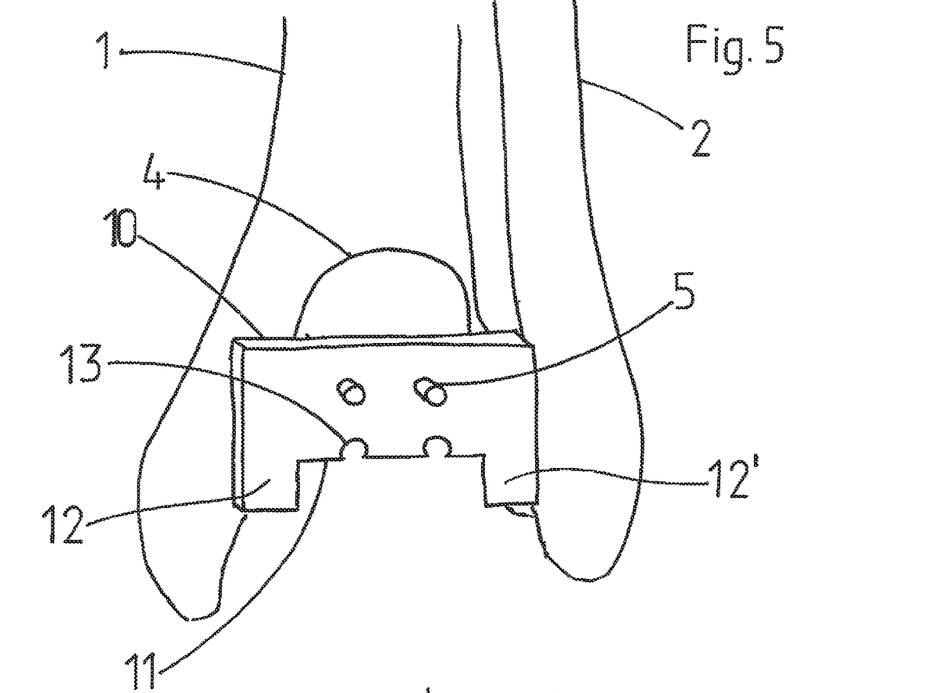
FIG. 5 shows a schematic rear view according to FIG. 3 with a joint-tensioning device pushed onto the base unit.

After a resection surface 1.2 has been produced on the shinbone 1, the saw jig 7 is taken off and replaced by a joint-tensioning device 10, which is realized by an elastomer body in FIGS. 5 to 10. The schematic rear view in FIG. 5 shows that the joint-tensioning device 10 has a shaft recess 11 into which a milling device can be inserted, and guide grooves 13 for a milling device are formed in the upper boundary face of the shaft recess 11. To the sides, the shaft recess 11 is delimited by support surfaces 12, 12' bearing on the ankle bone 3, which is not shown in FIG. 5.

Figure 6:
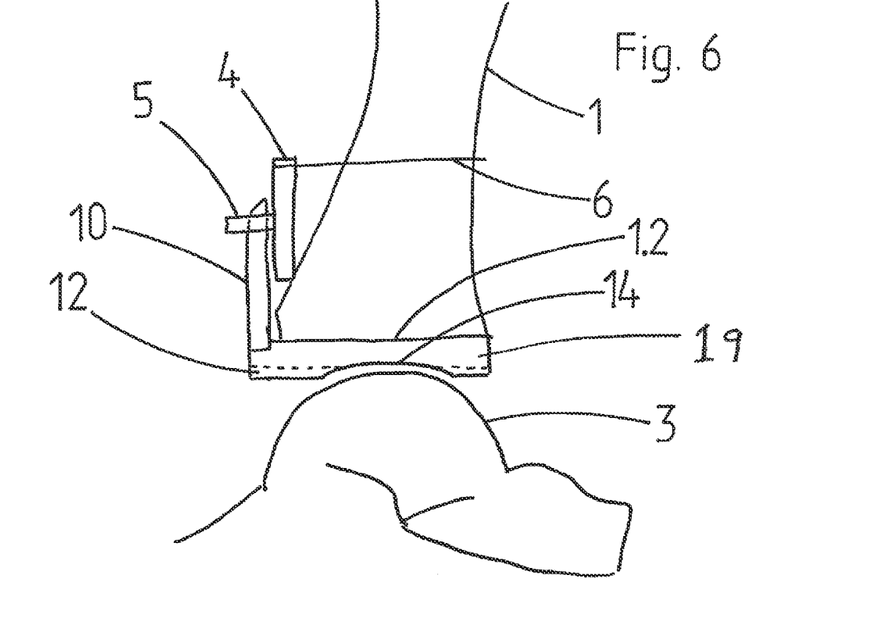
FIG. 6 shows a schematic side view of the arrangement according to FIG. 5.

In the side view according to FIG. 6, which corresponds to FIG. 5, it can be seen that the support surface 12 of the joint-tensioning device 10 has a concave curvature 14, which cooperates with the surface of the ankle bone 3. The concave curvature 14 avoids the ankle bone 3 sliding forward or backward during the resection but allows a swing-through of the ankle bone, that is to say a rotation of the ankle bone 3 relative to the shinbone 1. The concave curvature provides an abutment for the ankle bone 3 when the joint is swung through during the milling procedure.

It can likewise be seen in FIG. 6 that the resection surface 1.2 at the distal end of the shinbone, i.e. at the end away from the body, serves as a bearing surface for the part of the joint-tensioning device 10 pushed into the joint. The joint-tensioning device 10 has the effect that the elastomer body 10 bears only on the outer or inner component of the joint surface of the ankle bone, i.e. on the shoulders thereof. Between these, a defined space is left free, the shaft recess 11, which serves as work shaft.

By means of the elastomers, the ankle bone is oriented according to the natural joint tension, specifically in each position of the ankle joint. For this purpose, the elastomer body 10 cooperates with the ligaments of the ankle bone. The tension of the elastomer body is preferably such that the joint is oriented up to a specific maximum tension, but the material yields during swing-through if the joint tension exceeds a certain value. The joint-tensioning device 10 is designed with claws 19 which, in the state when inserted into a joint, bear on joint parts.

Figure 7:
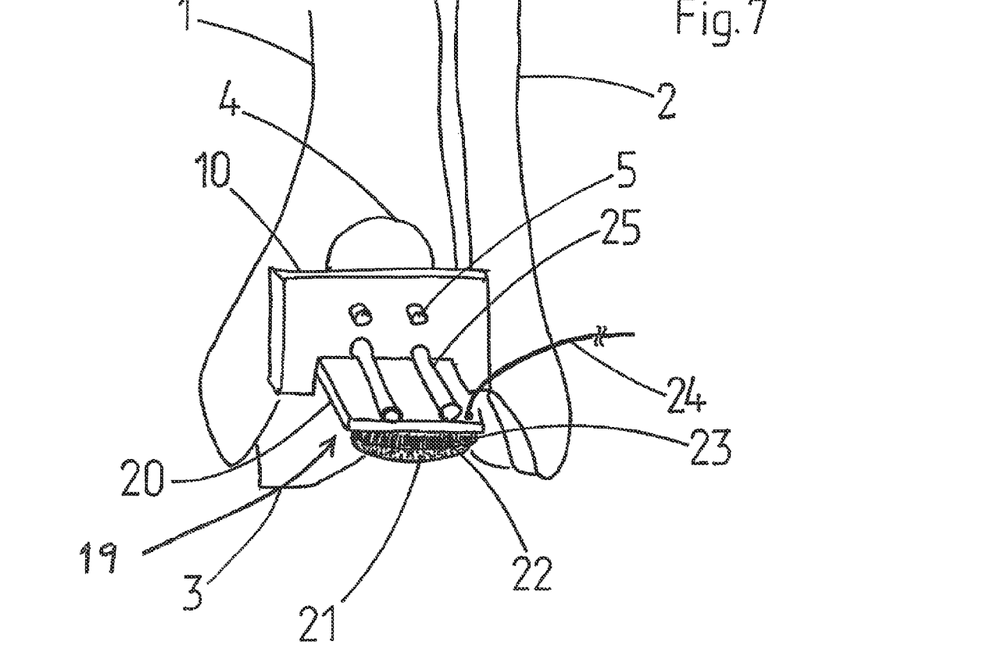
FIG. 7 shows a schematic rear view according to FIG. 3 with a device according to the invention, with a milling device before insertion into a joint-tensioning device.

FIG. 7 is a schematic rear view showing a milling device about to be pushed into the recess 11 of the joint-tensioning device 10. The milling device has a chassis 20, which has the same width as the recess 11. Guide bodies 25 are provided on the side of the chassis 20 facing toward the joint-tensioning device 10 and engage in the guide grooves 13 of the joint-tensioning device 10, and the milling device is mounted, guided and/or fixed in the joint-tensioning device 10 by means of these guide bodies 25.

On the side facing toward the ankle bone 3, the milling device has a face milling cutter 21, and, between the chassis 20 and the face milling cutter 21, it has a toothed wheel 22, which is arranged rotatably on the same axis as the face milling cutter 21. The toothed wheel 22 is, for example, formed in one piece with the face milling cutter 21. A smaller toothed wheel 23 is likewise arranged on the chassis 20 and meshes in the toothed wheel 22 of the face milling cutter 21. The toothed wheel 23 is driven by means of a spindle 24 of a drive device (not shown). The rotation axis of the toothed wheel 23 can be parallel to the rotation axis of the face milling cutter 21 and of the toothed wheel 22 or can be arranged at an angle thereto, for example at a right angle or 90° angle. FIGS. 7 to 10 also each show the knurling of the toothed wheels 22, 23.

Figure 8:
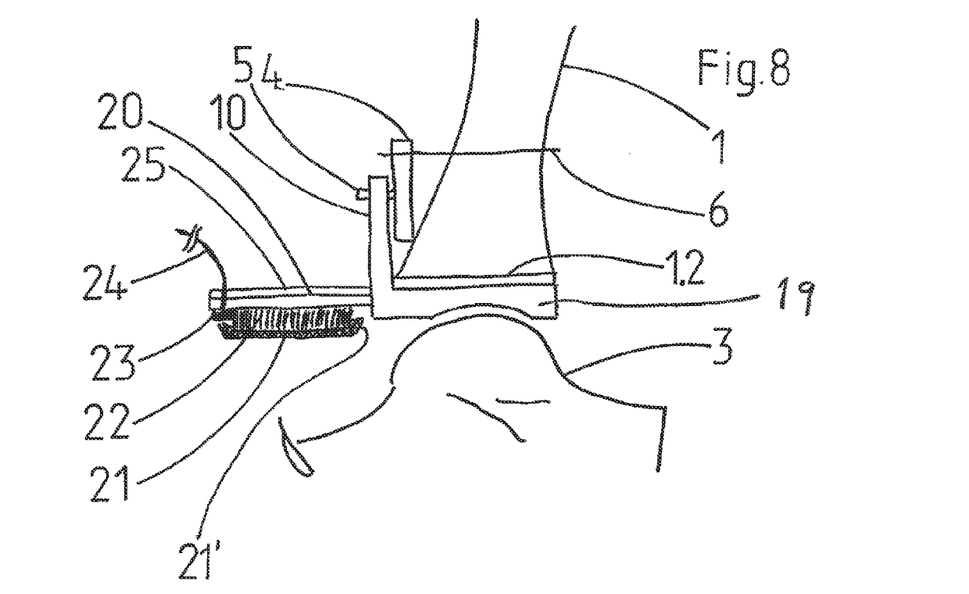
FIG. 8 shows a schematic side view of the arrangement according to FIG. 7.

FIG. 8 shows a schematic side view of the view according to FIG. 7. It can be seen that the face milling cutter 21 has a front milling surface and also angled lateral milling surfaces.

Figure 9:
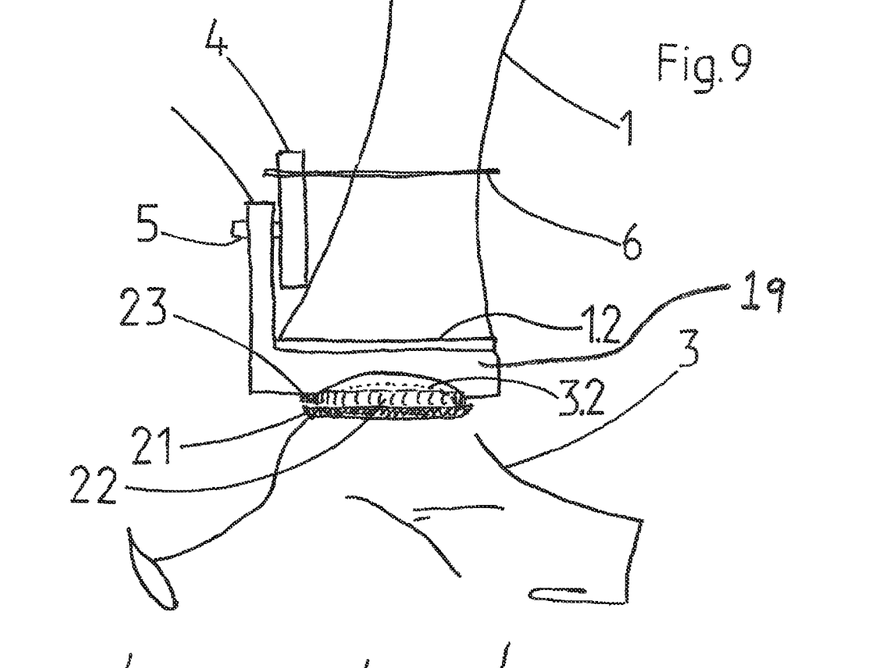
FIG. 9 shows a view according to FIG. 8 with inserted milling device, in a mid-position of the ankle joint.
Figure 10:
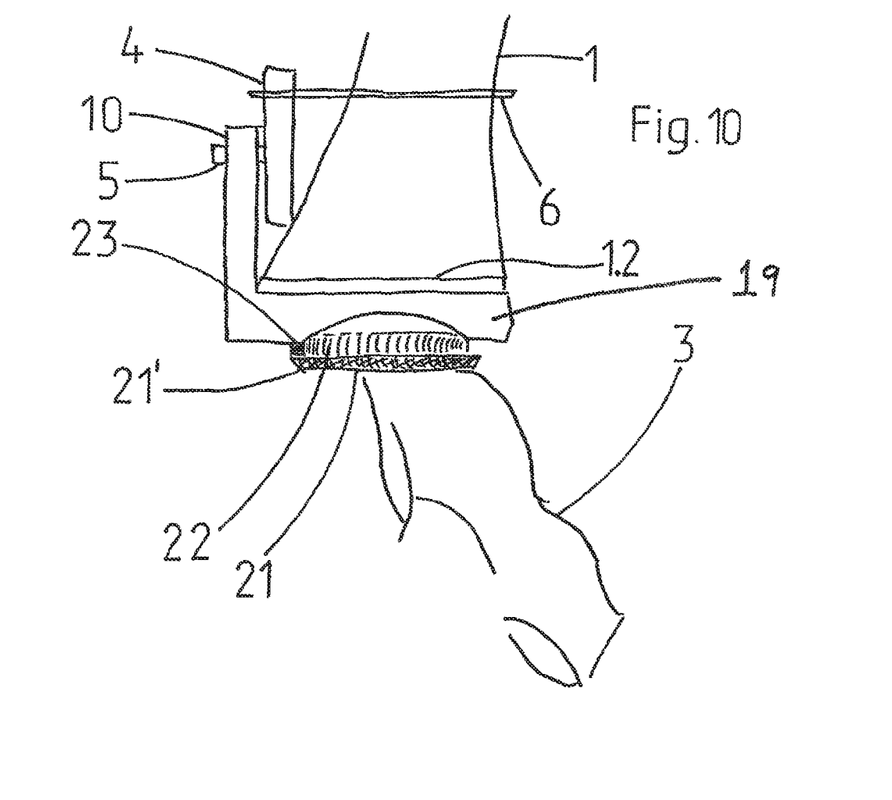
FIG. 10 shows a view according to FIG. 9 with the ankle joint swung through, FIG. 11 shows a schematic rear view of the partially resected ankle bone and shinbone.

FIGS. 9 and 10 show the milling device in the state when inserted into the joint-tensioning device 10. Even as the milling device is being inserted, the face miffing cutter 21 can be started up and thus generate a first part of a resection surface. FIGS. 9 and 10 are sectional views through a perpendicular plane through the ankle joint, approximately at the height of the pins 5. In FIG. 9, the ankle joint is shown in a neutral mid-position, while in FIG. 10 the ankle joint, represented merely by an ankle bone 3, has been brought to an end position. In this state, the ankle joint is tensioned by the elastomer body 10 and is held by the ankle-joint ligaments, such that the swing-through of the joint corresponds to the natural movement pattern. The resulting lower resection surface 3.3 on the ankle bone 3 thus corresponds ideally to the natural movement pattern of the ankle joint. The resection surface 3.3 is generated both by the face milling cutter 21 and also by the lateral milling surface 21' of the face milling cutter 21. Alternatively, the face milling cutter 21 is designed with a slight curvature.

Figures 11, 12:
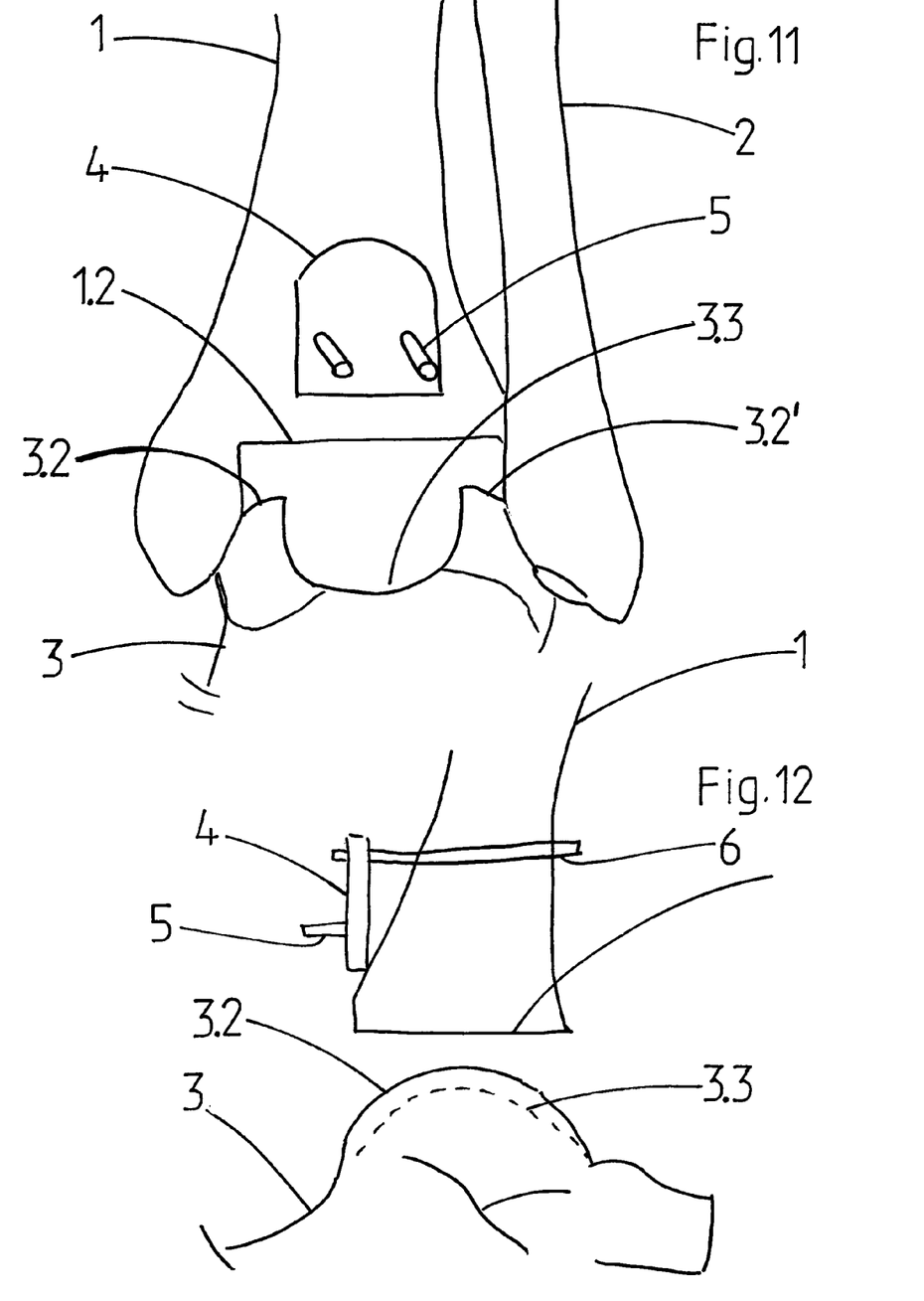

FIGS. 11 and 12 show a schematic rear view and schematic side view, respectively, of the partially resected ankle joint after removal of the joint-tensioning device 10. The ankle bone 3 has a central temporary resection surface 3.3 on the ankle bone 3, which resection surface 3.3 is curved. Situated to both sides of the temporary resection surface 3.3 there are lateral support arches 3.2, 3.2', on which the shinbone 1 and the calf bone 2 bear, respectively. In FIG. 12, the temporary resection surface 3.3 is shown by a broken line, the lateral support arch 3.2 by a solid line.

Figure 13:
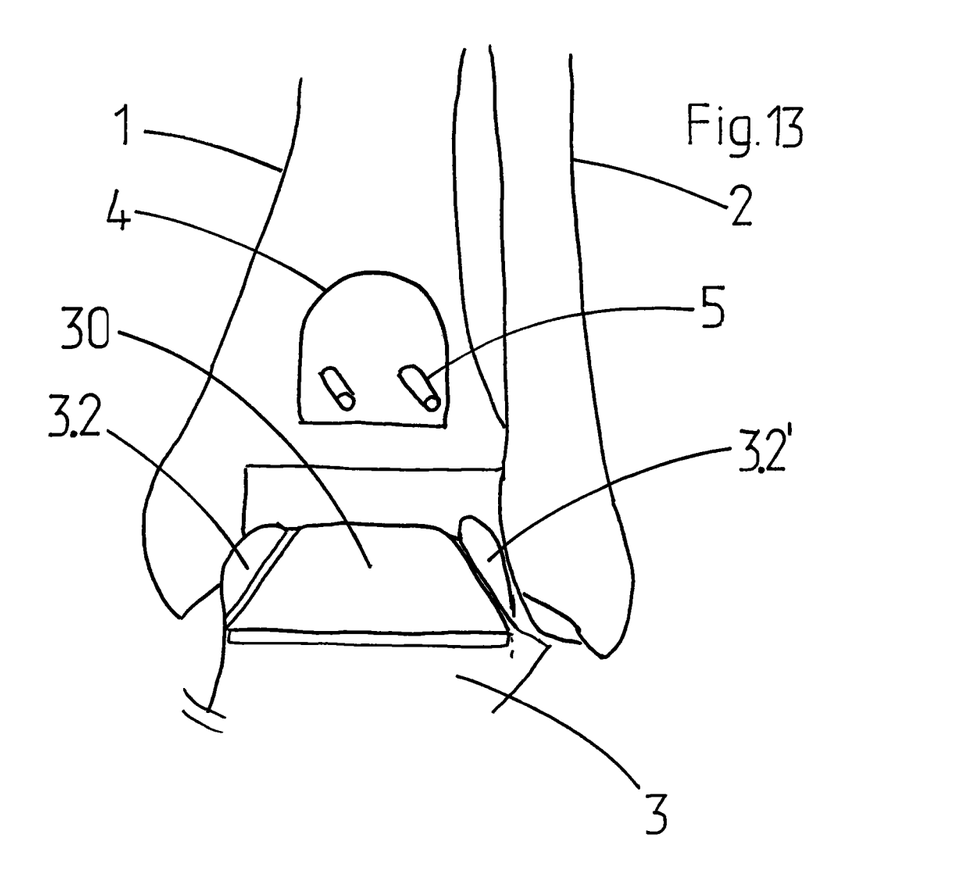
FIG. 13 shows the arrangement according to FIG. 11 with a curved saw jig inserted.

FIG. 13 shows, in a schematic rear view of the ankle joint, that a curved saw jig 30 has been placed on the temporary resection surface 3.3 on the ankle bone 3, the curvature of said saw jig 30 being adapted to the resection surface 3.3. The saw jig is used for guiding a saw by means of which the lateral support arches 3.2, 3.2' are removed.

Figure 14:
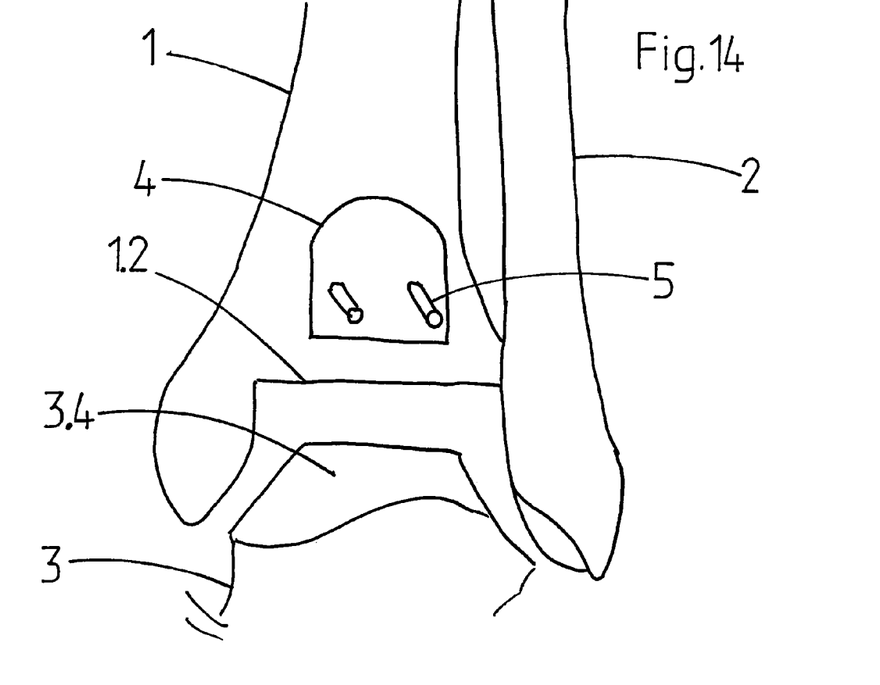
FIG. 14 shows a schematic rear view of an ankle joint with completely prepared resection surfaces.
Figure 15:
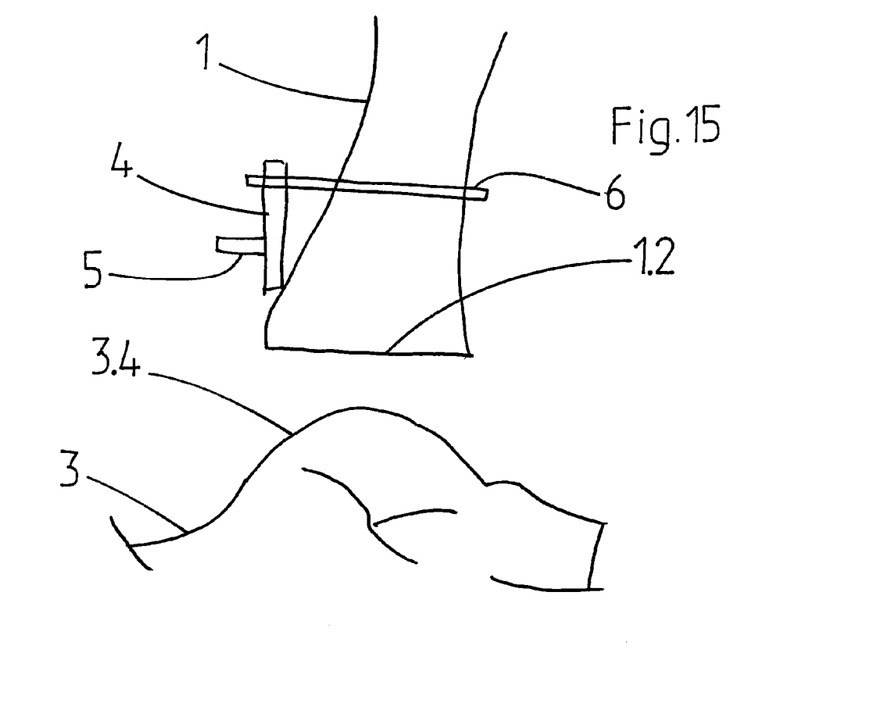
FIG. 15 shows a schematic side view of the arrangement according to FIG. 14.

The result of the subsequent removal of the lateral support arches is shown in a schematic rear view and side view, respectively, in FIG. 14 and FIG. 15. The ankle bone 3 now has a complete resection surface 3.4. Shinbone 1 and calf bone 2 no longer bear on the ankle bone 3, such that the ankle joint is now prepared such that endoprostheses can be implanted that replace the original joint surfaces. Since the generation of the resection surface 3.4 on the ankle bone 3 has been generated by swinging the joint through at a predetermined tension corresponding to a natural tension of the ligaments of the ankle joint, the generated resection surface 3.4 corresponds to the natural movement pattern dictated by the ligaments. The endoprostheses can also have this shape after their implantation.

All of the mentioned features, and also those only shown in the drawings, and also individual features disclosed in combination with other features, are regarded as essential to the invention both singly and in combination. Embodiments according to the invention can be realized by individual features or a combination of several features.

LIST OF REFERENCES 1 shinbone (tibia)
1.1 concave joint surface
1.2 resection surface on distal end of shinbone
2 calf bone (fibula)
3 ankle bone (talus)
3.1 convex joint surface
3.2, 3.2' lateral support arch
3.3 temporary resection surface on ankle bone
3.4 complete resection surface on ankle bone
4 base unit
5 pin
6 holder
7 saw jig
8 slit
10 joint-tensioning device
11 shaft recess
12, 12' support surface
13 guide groove
14 concave curvature
19 claws
20 chassis
21 face milling cutter
21' lateral milling surface
22 toothed wheel
23 toothed wheel
24 drive spindle
25 guide body
30 curved saw jig

The invention claimed is:
1. A device for in situ milling of joint surfaces, comprising:
a milling device; and
a joint-tensioning device,
wherein the joint-tensioning device is inserted between two joint components, the two joint components being bones, that form a joint, and press the joint components apart with a predetermined or adjustable tension,
wherein the joint-tensioning device has a recess into which the milling device can be inserted,
wherein the milling device has a face milling cutter,
wherein the joint-tensioning device includes claws which, in a state when inserted into the joint, bear on joint parts, and
wherein the joint-tensioning device is a one-piece or multi-piece elastomer body or comprises one or more elastomer bodies.
2. The device as claimed in claim 1, wherein the face milling cutter has milling surfaces both on its face and also on its periphery or has a curved milling profile.

3. The device as claimed in claim 1, wherein the milling device has a chassis for the face milling cutter, wherein the chassis can be inserted into the recess of the joint-tensioning device and/or can be fixed in the recess of the joint-tensioning device.

4. The device as claimed in claim 1, wherein the milling device can be driven by a gearwheel drive with toothed wheels, wherein one toothed wheel is connected to the face milling cutter or is formed in one piece with the face milling cutter, and another toothed wheel, which meshes in the toothed wheel connected to the face milling cutter or formed in one piece with the face milling cutter, is connected to a spindle.

5. The device as claimed in claim 4, wherein the spindle is connected to a drive device.

6. The device as claimed in claim 1, wherein the joint-tensioning device has a bearing surface for a resection surface of the bone.

7. The device as claimed in claim 1, wherein the recess of the joint-tensioning device has a shaft shape.

8. The device as claimed in claim 7, wherein the recess has means for mounting, guiding and/or fixing a milling device.

9. The device as claimed in claim 7, wherein to sides of the recess, the joint-tensioning device has support surfaces for supporting on the bone that is to be resected.

10. The device as claimed in claim 9, wherein the support surfaces have concave curvatures for receiving curved parts of the bone.

11. The device as claimed in claim 1, further comprising a base unit, which can be fixed on the bone and which has means for mounting the joint-tensioning device.

12. The device as claimed in claim 11, wherein the joint-tensioning device has openings or means for mounting on the base unit and/or for engagement with holding means of the base unit.

13. The use of the device as claimed in claim 1 for in situ milling of joint surfaces.

14. A method for in situ milling of joint surfaces with the device of claim 1, comprising the following method steps:
pushing the joint-tensioning device in between the joint components, adjacent to the joint, of which one joint component is already resected, wherein the joint is subjected to a predetermined or adjustable tension,
inserting the milling device with the face milling cutter into the recess of the joint-tensioning device, wherein the face milling cutter is driven during the insertion to form a resection surface on a hitherto non-resected joint component, and
producing a curved resection surface on the hitherto non-resected joint component by swinging the joint through once.

15. The method as claimed in claim 14, wherein a resection surface is produced beforehand on bone, by placing a base unit on the bone adjacent to the joint and mounting a saw jig onto the base unit.

16. The method as claimed in claim 15, wherein the saw jig is removed from the base unit after the resection surface has been produced on the bone.

17. The method as claimed in claim 14, wherein after the curved resection surface has been produced, the milling device and the joint-tensioning device are removed from the joint, and the joint components, on which the joint-tensioning device had previously rested, are removed.

18. The method as claimed in claim 17, wherein a final curved resection surface is obtained and/or a remaining joint component is completely covered with a prosthesis.

* * * * *